United States Patent [19]

Inagaki et al.

[11] Patent Number: 4,707,472

[45] Date of Patent: Nov. 17, 1987

[54] CYCLOARTENOL FERULATE/CYCLODEXTRIN COMPLEX

[75] Inventors: Tetsuya Inagaki; Hidemi Aoki; Hiroyasu Aikawa, all of Saitama; Masao Takahashi, Tokyo, all of Japan

[73] Assignee: Zeria Shinyaku Kogyo Kabushiki Kaisha, Tokyo, Japan

[21] Appl. No.: 845,134

[22] PCT Filed: Jun. 29, 1985

[86] PCT No.: PCT/JP85/00367

§ 371 Date: Feb. 28, 1986

§ 102(e) Date: Feb. 28, 1986

[87] PCT Pub. No.: WO86/00312

PCT Pub. Date: Jan. 16, 1986

[30] Foreign Application Priority Data

Jun. 30, 1984 [JP] Japan .............................. 59-136795

[51] Int. Cl.$^4$ ............................................ A61K 31/73

[52] U.S. Cl. ........................................ 514/58; 536/46; 536/103

[58] Field of Search ...................... 536/46, 103; 514/58

[56] References Cited

U.S. PATENT DOCUMENTS 4,352,793 10/1982 Yamahira et al. ..................... 514/58
4,407,795 10/1983 Nicolau et al. ........................ 514/58

Primary Examiner—J. R. Brown
Assistant Examiner—Elli Peselev
Attorney, Agent, or Firm—Scrivener and Clarke

[57] ABSTRACT

Cycloartenol ferulate/cyclodextrin complex is prepared by including cycloartenol ferulate, which is a component of γ-oryzanol and hardly soluble in water, with cyclodextrin to thereby elevate its solubility in water and improve its absorption through digestive tracts. Thus various pharmaceutical and physiological effects of cycloartenol ferulate are further improved.

5 Claims, 17 Drawing Figures

CYCLOARTENOL FERULATE/CYCLODEXTRIN COMPLEX

TECHNICAL FIELD

This invention relates to cycloartenol ferulate/cyclodextrin complex.

BACKGROUND ART

It has been known that hardly water-soluble pharmaceuticals will be ineffectively absorbed through digestive tracts. It is important to elevate the dissolution rate of these pharmaceuticals in order to improve these absorption through digestive tracts. Therefore it has been attempted to elevate the dissolution rate of hardly water-soluble pharmaceuticals to thereby improve the absorption of the same.

On the other hand, it is believed that cycloartenol ferulate, which is a component of γ-oryzanol, has antiarteriosclerotic, gonadotropic and antioxidant effects and is effective in treating various diseases including autonomic imbalance, hypertension and hepatic disorder.

However it is very difficult to isolate cycloartenol ferulate in high purity from γ-oryzanol. Further since cycloartenol ferulate is insoluble in water, it is ineffectively absorbed through digestive tracts and hardly transfers into blood when orally administered.

Thus it is believed that cycloartenol ferulate will insufficiently exert its pharmacological and physiological effects when administered alone or as a component of γ-oryzanol.

DISCLOSURE OF THE INVENTION

It is an object of the present invention to overcome the above problem that cycloartenol ferulate is hardly soluble in water so that it is ineffectively absorbed through digestive tracts and exerts its pharmacological and physiological effects insufficiently, by improving the absorption of the same through digestive tracts to thereby elevate its pharmacological and physiological effects.

As a result of our studies, we have confirmed the formation of a complex of cycloartenol ferulate with cyclodextrin. We have further found that the formation of said complex will elevate the dissolution rate of cycloartenol ferulate and improve the absorption of the same through digestive tracts in animal tests, thus completing the present invention.

Accordingly the present invention relates to a cycloartenol ferulate/cyclodextrin complex which comprises cycloartenol ferulate included with cyclodextrin.

Cycloartenol ferulate as mentioned herein may be isolated from γ-oryzanol and purified, e.g., in the following manner.

That is, 500 g of γ-oryzanol is dissolved in 1.5 to 2.0 l of heated chloroform and methanol is added thereto until crystals separate out. The mixture is heated again to thereby dissolve the crystals and then allowed to stand at room temperature. Thus crystals separate out. The crystals thus obtained are washed with n-hexane. 100 g of the resulting crude cycloartenol ferulate is dissolved in chloroform, absorbed by a reverse phase column packing and developed with methanol/-chloroform/water at a volume ratio of 6:2:1. Main fractions are combined and the solvent is distilled off therefrom. The residue is recrystallized from chloroform/methanol at a volume ratio of 1:1 to thereby give 60 g of cycloartenol ferulate.

Cycloartenol ferulate thus obtained is identified by high-performance liquid chromatography (HPLC), mass spectrometry (MS), infrared spectroscopy (IR) and nuclear magnetic resonance spectroscopy (NMR).

Thus its HPLC shows a single peak as shown in FIG. 1.

Its MS shows a molecular ion peak (602) of cycloartenol ferulate as shown in FIG. 2.

Its IR shows a streching vibration of C=O at 1670 cm$^{-1}$, vibrations of methyl groups at 1470 cm$^{-1}$ to 1430 cm$^{-1}$ and at 1380$^{-1}$ to 1350 cm$^{-1}$ and characteristic vibration pattern of a cyclopropane ring at 1020 cm$^{-1}$ as shown in FIG. 3. Its NMR shows signals of a cyclopropane ring, an —OCH$_3$ group, a hydroxyl group of phenol and

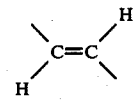

at δ values of 0.58 ppm, 3.92 ppm, 5.92 ppm, and 6.15 ppm and 7.47 ppm, respectively as shown in FIG. 4. Furthermore it shows a signal of

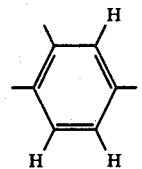

at 6.93 ppm.

These results prove that the product is cycloartenol ferulate.

Available cyclodextrins include α-cyclodextrin, β-cyclodextrin, γ-cyclodextrin, 2,6-di-O-methyl-β-cyclodextrin, α-cyclodextrin polymer, β-cyclodextrin polymer and γ-cyclodextrin polymer.

β-Cyclodextrin as mentioned above comprises seven glucose units bonded together to thereby form a ring. Two hydroxyl groups (-OH) at the 2 and 6-positions among three of each glucose unit are methylated (—OCH$_3$) to give 2,6-di-O-methyl-β-cyclodextrin. β-Cyclodextrin polymer is a polymer which is obtained by reacting β-cyclodextrin with epichlorhydrin reagent in an alkaline solution and has a network structure wherein 3 to 10 β-cyclodextrin molecules are crosslinked together. α-Cyclodextrin and γ-cyclodextrin polymers may be similarly obtained.

Now a process for the formation of a cycloartenol ferulate/cyclodextrin complex will be described.

Cycloartenol ferulate and cyclodextrin are introduced into a vessel and concentrated aqueous solution of ammonia is added thereto. After stirring the mixture, aqueous solution of ammonia is completely vaporized off under reduced pressure to thereby give the aimed complex.

The amount of cyclodextrin as used herein is variable and aqueous solution of ammonia may be substituted by ethanol in the same procedure.

Now the identification of the formation of the cycloartenol ferulate/cyclodextrin complex will be described.

An UV absorption spectrum of cycloartenol ferulate/β-cyclodextrin polymer complex is compared with that of cycloartenol ferulate.

As a result, cycloartenol ferulate alone shows an absorption maximum at 320 nm and a molecular absorptivity of 15000, while the complex shows an absorption maximum at 330 nm and an increased molecular absorptivity of 19000, as shown in FIG. 5.

As a result of differential thermal analysis, cycloartenol ferulate alone shows obvious endothermic peaks around 150° C. as shown in FIGS. 8 and 9. On the other hand, the complex shows no peak around 150° C. but a gentle differential thermal analysis curve as shown in FIG. 10. These facts suggest that β-cyclodextrin polymer and cycloartenol ferulate exert interactions with each other, which proves the formation of the complex.

The formation of cycloartenol ferulate/2,6-di-O-methyl-β-cyclodextrin complex is identified in the similar manner. As shown in FIG. 6, the complex shows an absorption maximum at longer wavelength, i.e. 330 nm, than cycloartenol ferulate alone and also shows an increased molecular absorptivity, i.e. 19000. As a result of differential thermal analysis, the complex shows no endothermic peak around 150° C., which is observed in cycloartenol ferulate alone, but a gentle curve, as shown in FIG. 11. This curve shows a pattern different from that observed in cycloartenol ferulate/β-cyclodextrin polymer complex. These facts proves the formation of the complex.

Cycloartenol ferulate/β-cyclodextrin complex is examined as follows. An UV absorption spectrum of the complex shows an absorption maximum at longer wavelength, i.e. 330 nm, than cycloartenol ferulate alone. It also shows an increased molecular absorptivity, i.e. 19000.

This result proves the formation of cloartenol ferulate/β-cyclodextrin complex.

As stated previously, it is important to elevate the dissolution rate of a hardly water-soluble pharmaceutical in order to improve its absorption through digestive tracts.

Thus we have examined the effect of the cycloartenol ferulate/cyclodextrin complex on the dissolution rate in the following manner.

200 ml portions of water are introduced into two beakers. 40 mg of cycloartenol ferulate is added to one beaker. Separately an equivalent amount, i.e. corresponding to 40 mg of cycloartenol ferulate, of a cycloartenol ferulate complex is added to the other beaker. Each mixture is stirred at by a stirrer (150 rpm) to make the concentration of the content in the beaker uniform at 25° C. This temperature is maintained throughout the test. 4 ml portions of the content are collected at a specified interval and the absorbance of each sample is determined. The water in the beaker is adjusted to 200 ml each time a sample is collected.

The absorbance is determined by subtracting the absorbance at 400 nm from that at the isoabsorption point (305 nm) obtained from the UV absorption spectrum in the formation of the complex. The isoabsorption point refers to the wavelength of UV absorptions of cycloartenol ferulate alone and in the formation of the cycloartenol ferulate/cyclodextrin complex, while the wavelength of 400 nm refers to the one at which the UV absorption of cycloartenol ferulate disappears.

Thus the data at 400 nm refers to that of cycloartenol ferulate which is actually not dissolved in water. Therefore the dissolution rate in water can be accurately determined by subtracting the absorbance at 400 nm from that at 305 nm. FIG. 12 shows the dissolution rate determined in the above manner.

As a result, it is found that cycloartenol ferulate shows no absorption during the first 60 min., which shows that it is completely insoluble in water.

In contrast, the cycloartenol ferulate/β-cyclodextrin complex shows an increase in the absorbance to 0.20 after 30 min. accompanied by an increase in the dissolution rate.

Further cycloartenol ferulate/2,6-di-0-methyl-β-cyclodextrin complex shows an increase in the absorbance to approximately 0.40 after 10 min. accompanied by an increase in the dissolution rate.

Furthermore cycloartenol ferulate/β-cyclodextrin polymer complex shows an increase in the absorbance to approximately 0.60 after 10 min. and to approximately 0.70 after 15 min. accompanied by a significant improvement in the dissolution rate.

Further α-cyclodextrin polymer and γ-cyclodextrin polymer complexes also show respectively a significant improvement in the dissolution rate.

Furthermore cycloartenol ferulate complexes with α-cyclodextrin and γ-cyclodextrin prepared by the use of ethanol as described in Preparation Examples hereinafter show respectively a significant increase in the dissolution rate as shown in FIG. 13.

Cycloartenol ferulate complexes with polymers such as polyvinylpyrrolidone (PVP) and polysaccharides such as pullulan are similarly subjected to the above dissolution rate test. As a result, it is found that each complex shows a smaller increase in the dissolution rate than that observed with the use of various cyclodextrins (see FIG. 12). Each complex used in the above test comprises cycloartenol ferulate and cyclodextrin at a weight ratio of 1:3.

The ratio of cycloartenol ferulate to cyclodextrin in the formation of a cyclodextrin complex is examined with β-cyclodextrin polymer complex. Consequently it is found that the dissolution rate increases with an increase in the amount of β-cyclodextrin polymer in the complex, as shown in FIG. 14.

Thus the ratio of cycloartenol ferulate to cyclodextrin in the formation of a cycloartenol ferulate/cyclodextrin complex may be varied.

As described above, the dissolution rate can be significantly elevated by forming complexes of cycloartenol ferulate with various cyclodextrins.

The following experimental example shows that the cycloartenol ferulate whose solubility is significantly elevated by forming the same into a complex with cyclodextrin will exert various pharmaceutical effects when absorbed.

We have found that the absorbed cycloartenol ferulate decreases the amount of dopamine contained in the hypothalamus.

Thus cycloartenol ferulate complexes with various cyclodextrins and cycloartenol ferulate alone are orally administered to rats in a dose of 16.5 mg/kg and 50.0 mg/kg (in terms of cycloartenol ferulate) to examine a possible improvement in the absorption of cycloartenol ferulate with the guidance of a decrease in the dopamine content in the hypothalamus.

The result shows that administration of 16.5 mg/kg and 50.0 mg/kg of cycloartenol ferulate brings about decreases in the dopamine content in the hypothalamus of 18.6% and 14.1%, respectively, as compared with the control group. On the other hand, administration of the cycloartenol ferulate/β-cyclodextrin complex, cycloartenol ferulate/γ-cyclodextrin complex and cycloartenol ferulate-/β-cyclodextrin polymer complex brings about decreases in dopamine content of 28.1% and 30.5%, 38.8% and 42.9%, and 48.6% and 51.3%, respectively, each depending on the dose (see FIGS. 15 and 16).

We have further found that cycloartenol ferulate absorbed through digestive tracts will exhibit an antistress ulcer effect.

Thus cycloartenol ferulate alone and cycloartenol ferulate/γ-cyclodextrin complex are orally administered to rats which are under stress by immersing in water. Then the length of spot and linear ulcers observed in the stomach of each animal are measured and the sum thereof is referred to as an ulcer index. The ulcer inhibition ratio determined by the following equation with the use of the ulcer index is employed as an indication of the improvement in the absorption of cycloartenol ferulate:

$$\frac{\text{ulcer index of control group} - \text{ulcer index of test group}}{\text{ulcer index of control group}} \times 100\%$$

Consequently the control group shows an ulcer index of 37.95 mm, the group to which 300 mg/kg of cycloartenol ferulate is administered shows that of 34.00 mm and the group to which 600 mg/kg of the cycloartenol ferulate/γ-cyclodextrin complex (corresponding to 100 mg/kg of cycloartenol ferulate) is administered shows that of 25.55 mm. As shown in FIG. 17, the group to which 300 mg/kg of cycloartenol ferulate is administered shows an ulcer inhibition ratio of 10.4% compared with the control group. On the other hand, the group to which 600 mg/kg of the cycloartenol ferulate/γ-cyclodextrin complex (corresponding to 100 mg/kg of cycloartenol ferulate) is administered shows that of 32.7%.

The above experiment proves that the absorption of cycloartenol ferulate through digestive tracts is improved by forming the same into a complex with cyclodextrin and that the dissolution rate of cycloartenol ferulate is correlative to the absorption of the same through digestive tracts.

An improvement in the absorption of cycloartenol ferulate through digestive tracts is confirmed as described above referring to the animal test, so that it is expected that the pharmacological and physiological effects of the same are similarly improved thereby.

Since it has been proved that cyclodextrin and its derivatives may form a complex with cycloartenol ferulate, the compounds having a very similar structure to that of cycloartenol ferulate, such as cyclobranol ferulate, cyclobranol, cycloartenol, 24-methylenecycloartanol ferulate and 24-methylenecycloartanol also may similarly form a complex with cyclodextrins.

BRIEF DESCRIPTION OF THE DRAWINGS

FIG. 1 is a pattern chart obtained by high-performance liquid chromatography, FIG. 2 is a mass spectrum, FIG. 3 is an infrared spectrum and FIG. 4 is a nuclear magnetic reasonance spectrum.

FIG. 5 shows a comparison of cycloartenol ferulate/β-cyclodextrin polymer complex with cycloartenol ferulate, FIG. 6 shows a comparison of cycloartenol ferulate/2,6-di-O-methyl-β-cyclodextrin complex with cycloartenol ferulate and FIG. 7 shows a comparison of cycloartenol ferulate/β-cyclodextrin complex with cycloartenol ferulate.

FIG. 8 is that of cycloartenol ferulate, FIG. 9 is that of cycloartenol ferulate stirred in aqueous solution of ammonia, FIG. 10 is that of cycloartenol ferulate/β-cyclodextrin polymer complex and FIG. 11 is that of a cycloartenol ferulate/2,6-di-0-methyl-β-cyclodextrin complex.

Figure 1:
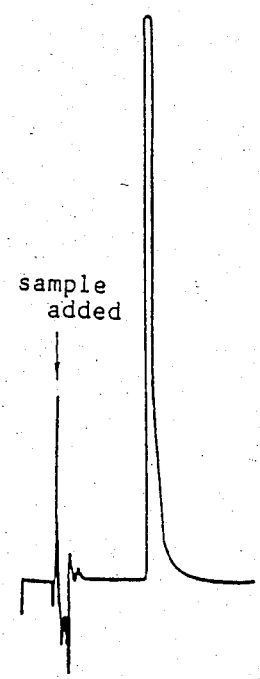
FIGS. 1 to 4 are various spectra of cycloartenol ferulate, which is a component of the complex of the present invention, where
Figure 2:
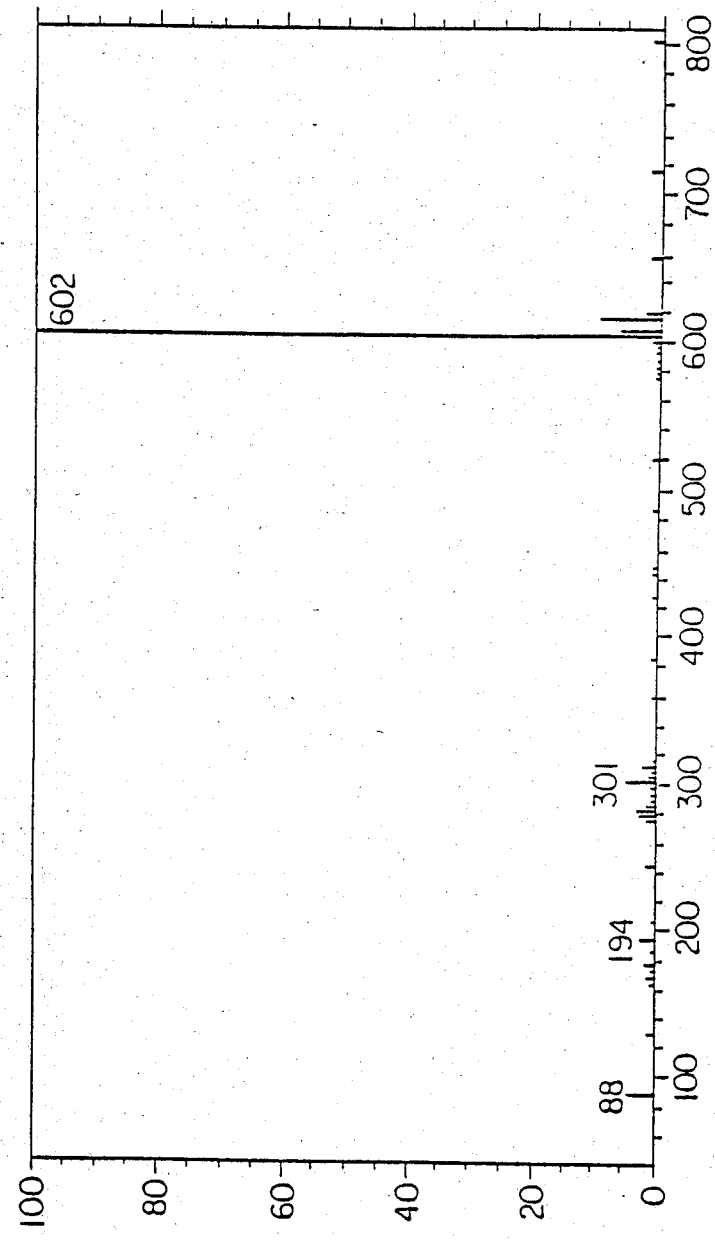
Figure 3:
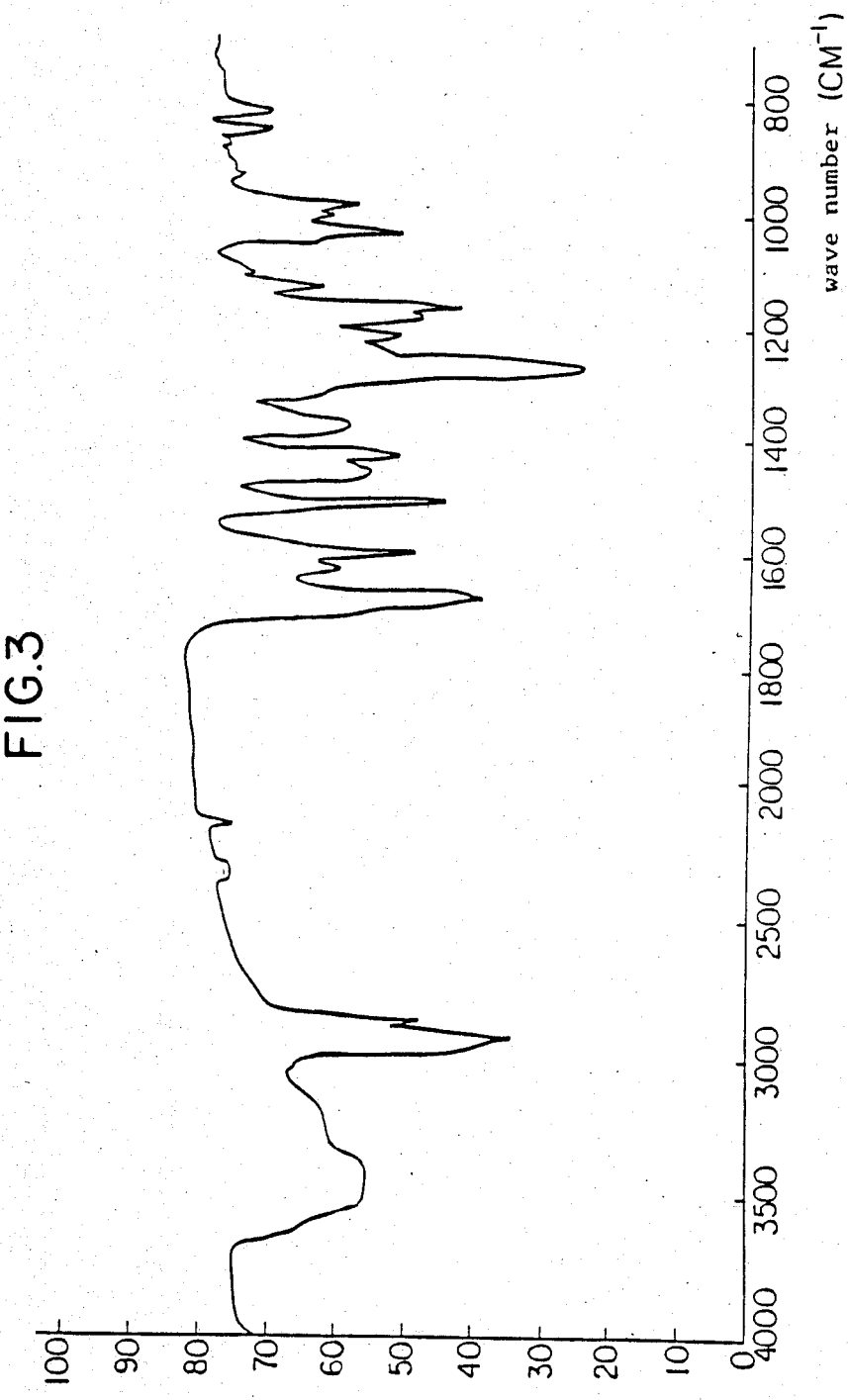
Figure 4:
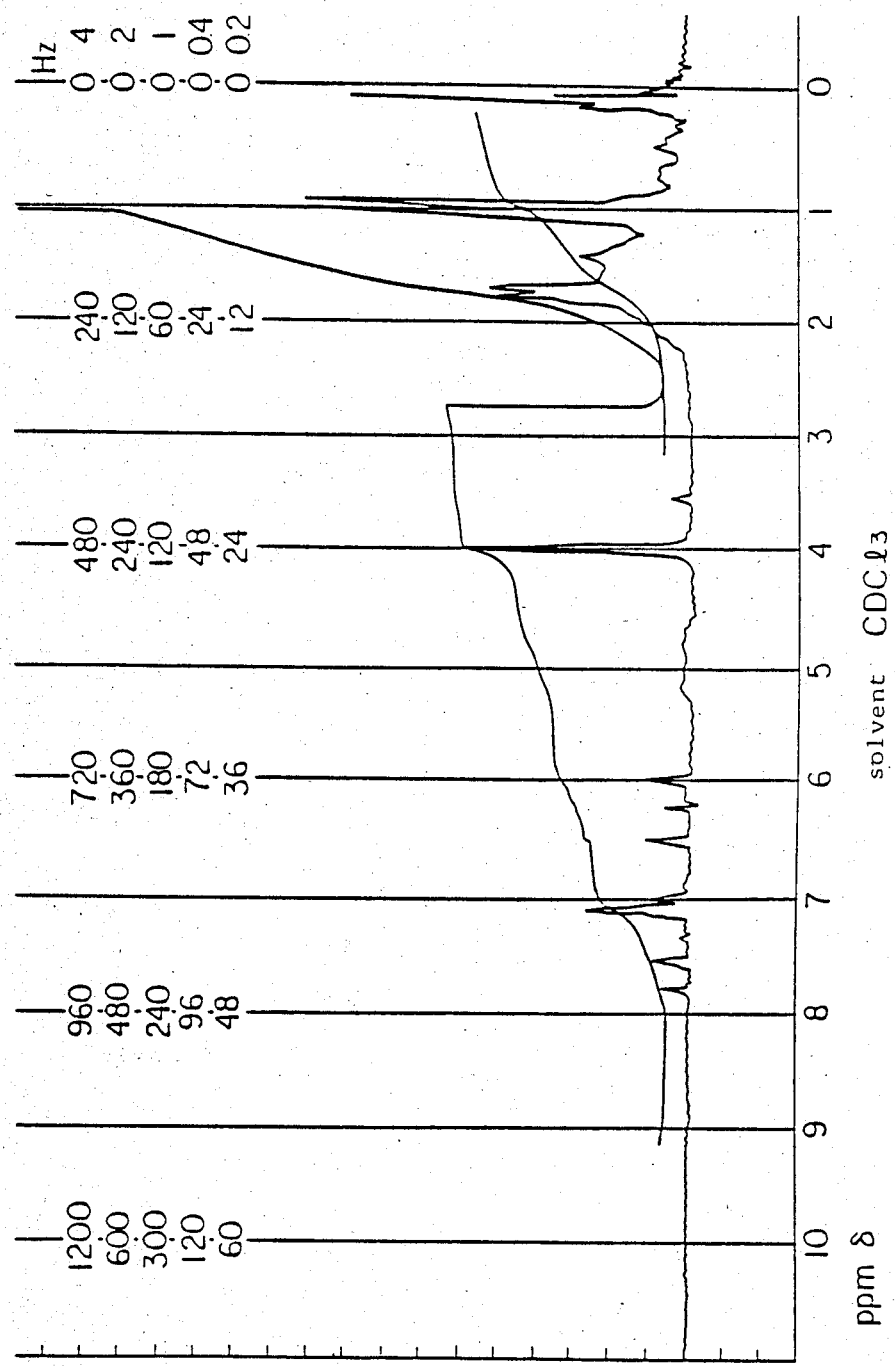
Figure 5:
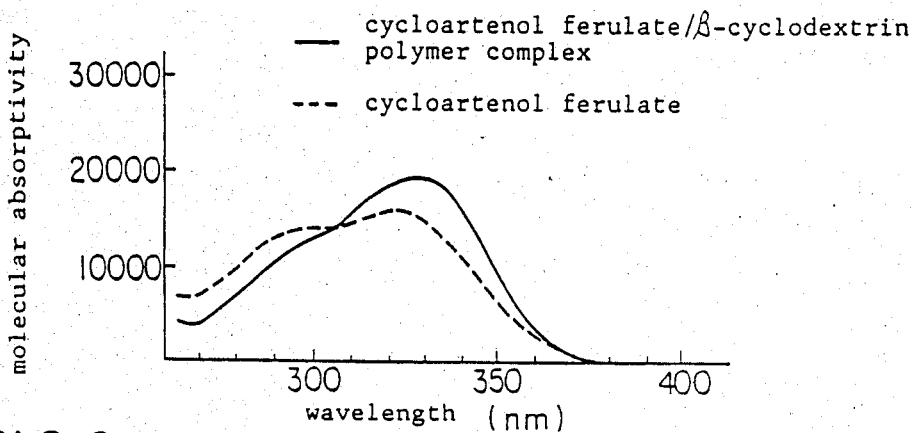
FIGS. 5 to 7 are given to compare UV absorption spectra of the complexes of the present invention with that of cycloartenol ferulate, where
Figure 6:
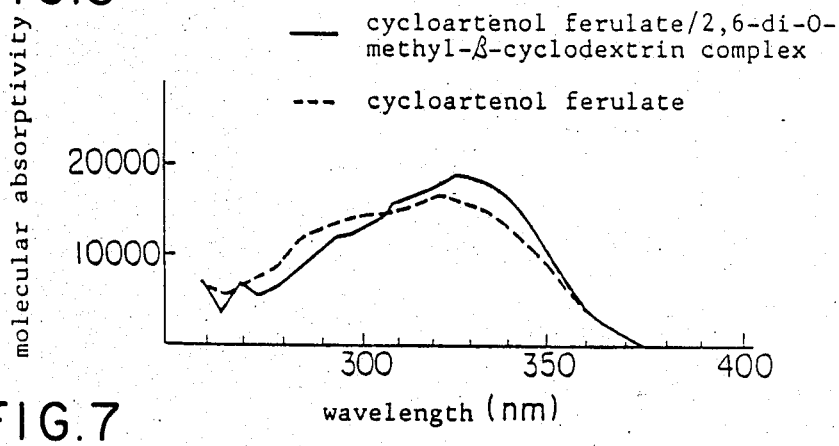
Figure 7:
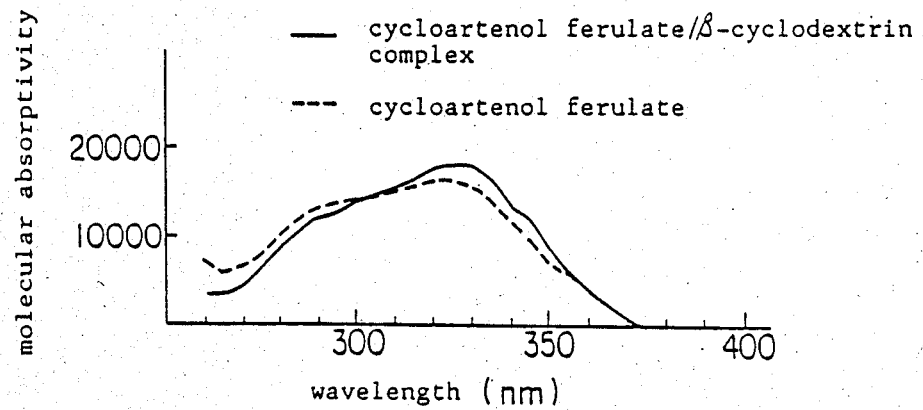
Figure 8:
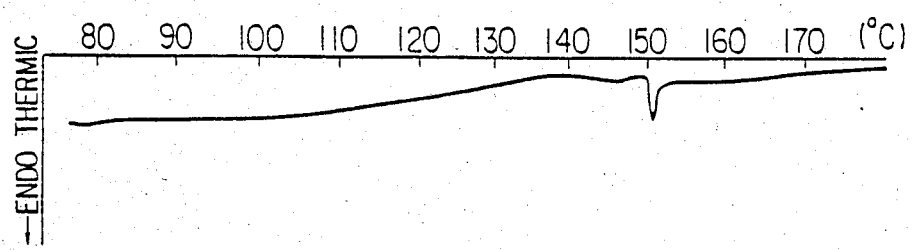
FIGS. 8 to 11 are pattern charts obtained by differential thermal analysis, where
Figure 9:
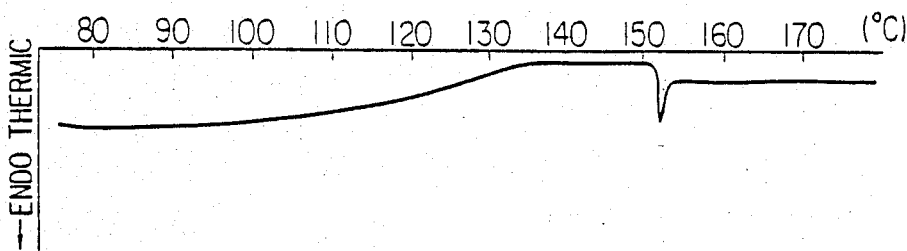
Figure 10:
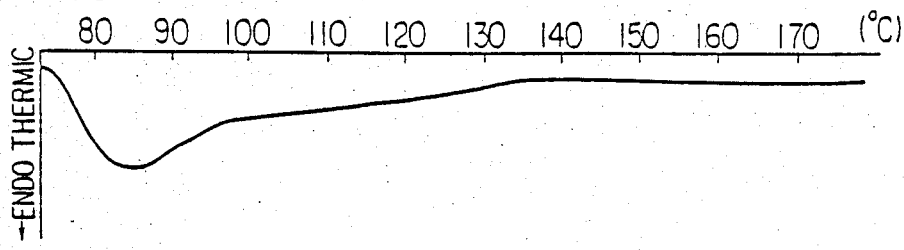
Figure 11:
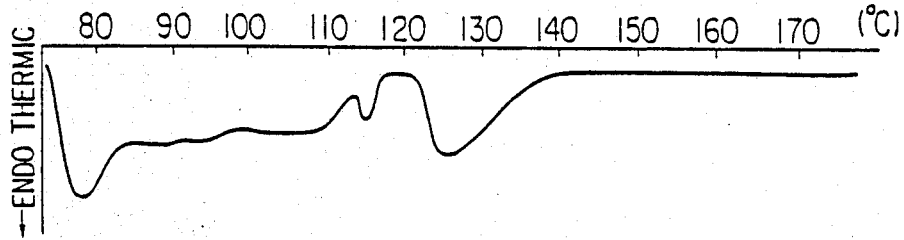
Figure 12:
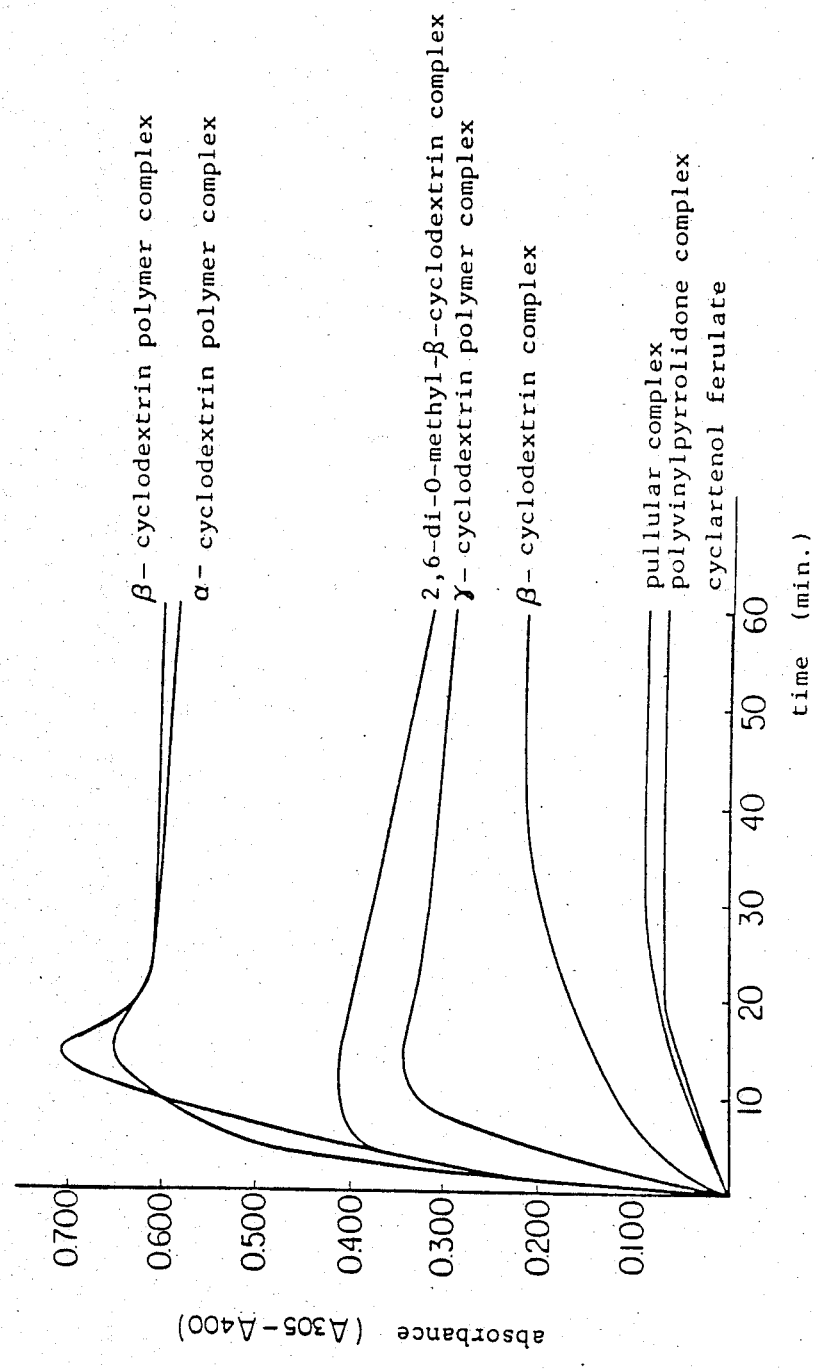
FIG. 12 shows the dissolution rate of a complex of the present invention prepared with aqueous solution of ammonia.
Figure 13:
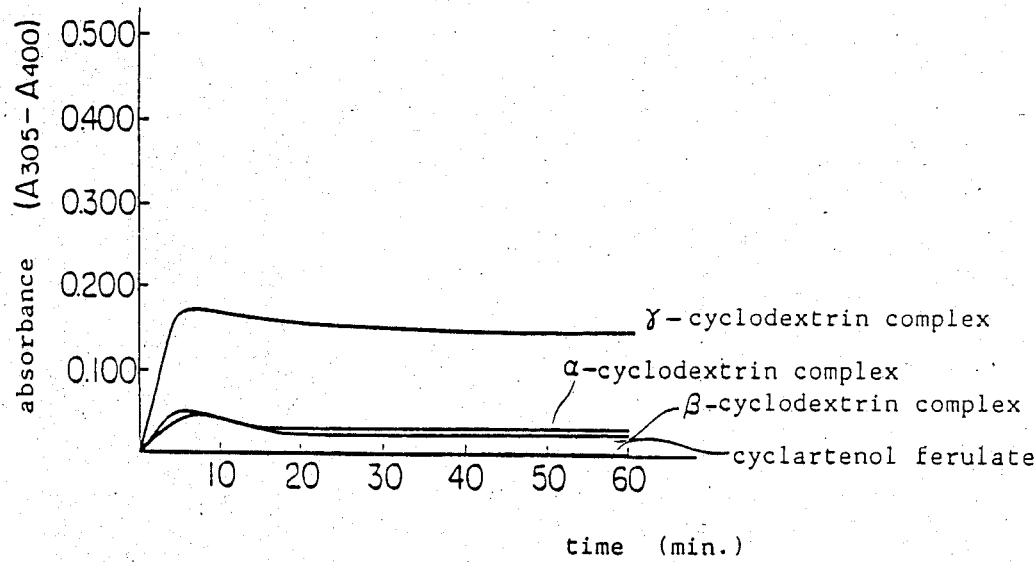
FIG. 13 shows the dissolution rate of a complex of the present invention prepared with ethanol.
Figure 14:
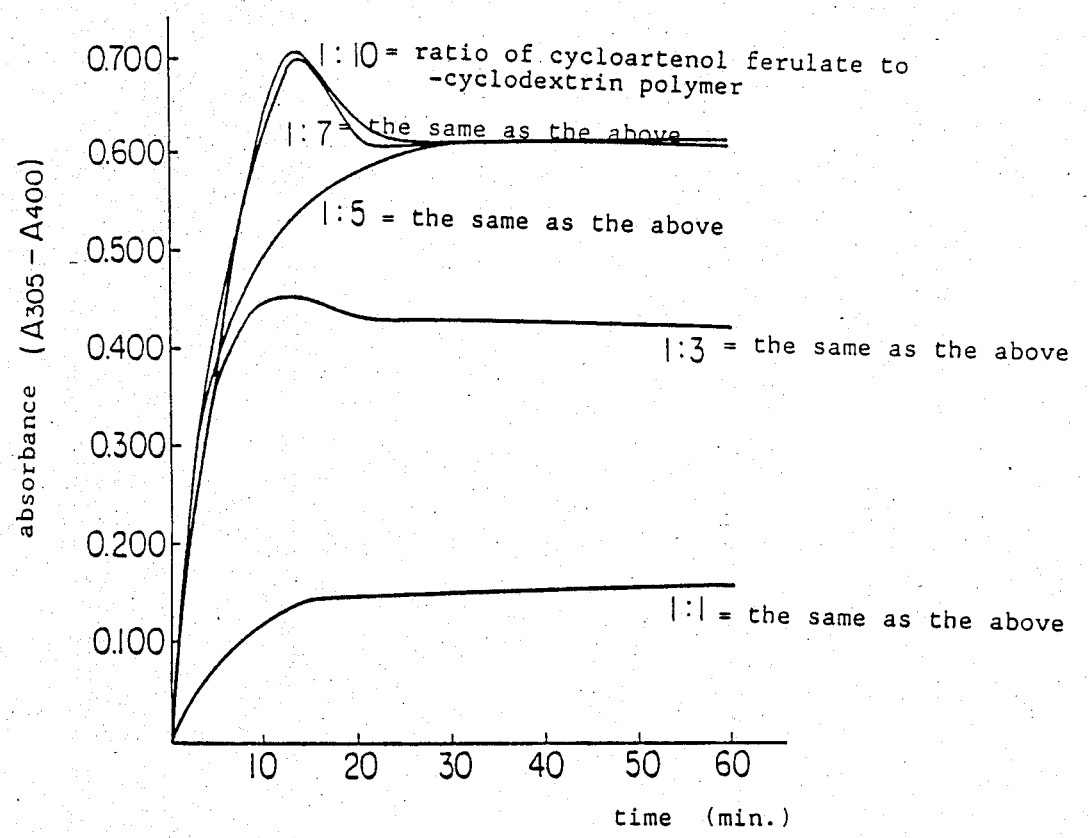
FIG. 14 shows effects of β-cyclodextrin polymer content in cycloartenol ferulate/β-cyclodextrin polymer complexes on the dissolution rate.
Figure 15:
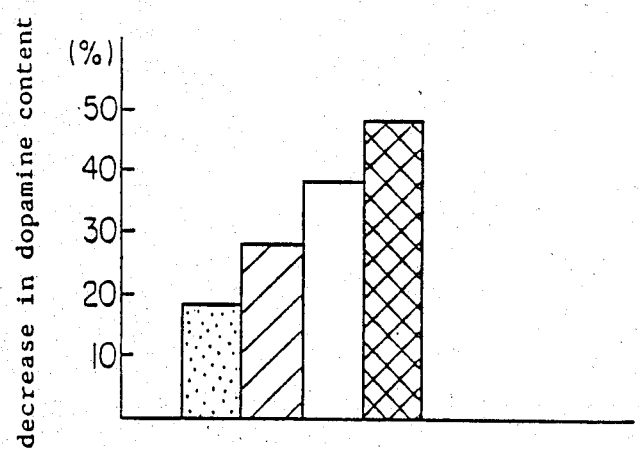
FIGS. 15 and 16 show the effects of the complexes of the present invention on decreasing the dopamine content. Each complex is administered in doses of 16.5 mg/kg and 50.0 mg/kg based on cycloartenol ferulate in FIGS. 15 and 16, respectively.
Figure 16:
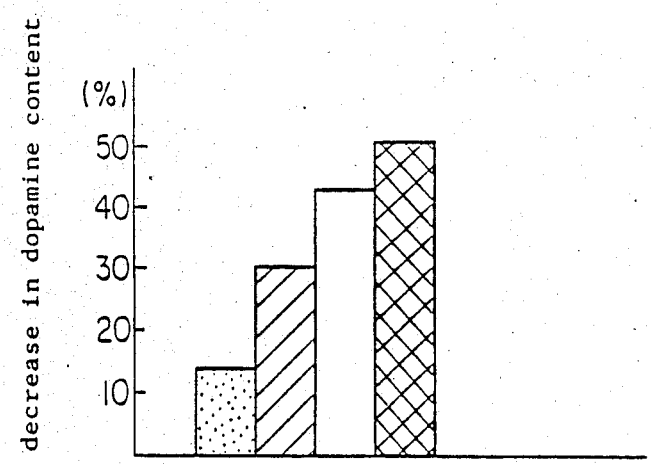
Figure 17:
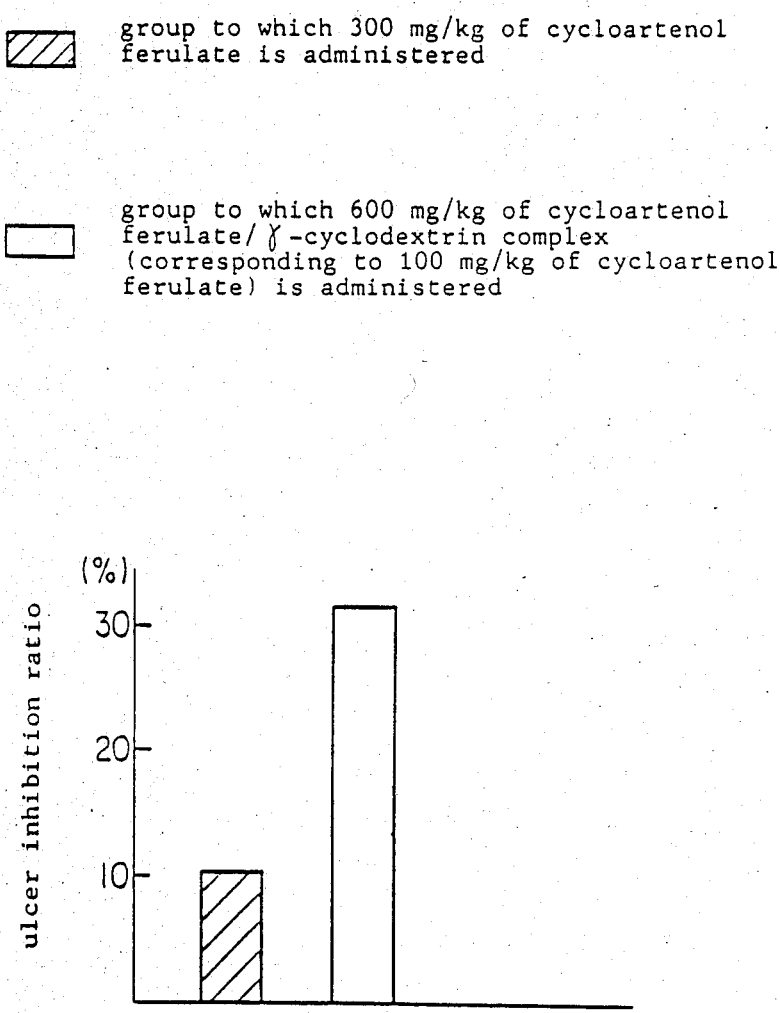
FIG. 17 shows an ulcer inhibition ratio of a cycloartenol ferulate/γcyclodextrin complex.

BEST MODE FOR CARRYING OUT THE INVENTION 40 mg of cycloartenol ferulate and 120 mg of cyclodextrin are introduced into a vessel and approximately 5 ml or more of 28% aqueous solution of ammonia is added thereto. The mixture is stirred for 60 min. or longer to thereby form a complex. After completely vaporizing aqueous solution of ammonia off under the reduced pressure, a cycloartenol ferulate/cyclodextrin complex is obtained.

The amount of cyclodextrin as used herein may be varied and aqueous solution of ammonia may be substituted by ethanol in the same procedure.

When the cycloartenol ferulate and cyclodextrin complex thus prepared is administered as autonomic modifier to human body, such administration is made orally in a dose of 0.01 to 5 g (0.002 to 2 g in terms of cycloartenol ferulate), preferably 0.1 to 5 g (0.02 to 2 g in terms of cycloartenol ferulate) per adult per day.

CAPABILITY OF EXPLOITATION IN INDUSTRY

As described above, cycloartenol ferulate, which has various pharmaceutical and physiological effects but insufficiently exerts these effects since it is hardly soluble in water, can be made soluble in water by forming the same into a cycloartenol ferulate/cyclodextrin complex of the present invention. Thus the absorption of cycloartenol ferulate through digestive tracts is improved and it is expected that the various excellent pharmaceutical and physiological effects of the same may be further elevated thereby.

What is claimed is:

1. A composition for improving the bioavailability of cycloartenol ferulate comprising a complex of cycloartenol ferulate and cyclodextrin in a weight ratio of 1:3.

2. The composition of claim 1 wherein the cyclodextrin is selected from the group consisting of α-cyclodextrin, β-cyclodextrin and γ-cyclodextrin.

3. A composition for improving the bioavailability of cycloartenol ferulate comprising a complex of cycloartenol ferulate and 2,6-di-O-methyl-β-cyclodextrin in a weight ration of 1:3.

4. A composition for improving the bioavailability of cycloartenol ferulate compirsing a complex of cycloartenol ferulate and cyclodextrin polymer in a weight ratio of 1:1 to 10.

5. The composition of claim 4 wherein said cyclodextrin polymer is selected from the group consisting of α-cyclodextrin polymer, β-cyclodextrin polymer and γ-cyclodextrin polymer.

* * * * *